(12) United States Patent
Choo et al.

(10) Patent No.: US 12,221,412 B2
(45) Date of Patent: Feb. 11, 2025

(54) SYSTEM AND METHOD FOR PRODUCING DIESTER-BASED COMPOSITION

(71) Applicant: LG CHEM, LTD., Seoul (KR)

(72) Inventors: Yeon Uk Choo, Daejeon (KR); Sung Kyu Lee, Daejeon (KR); Jae Hun Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 636 days.

(21) Appl. No.: 17/613,868

(22) PCT Filed: Sep. 10, 2020

(86) PCT No.: PCT/KR2020/012231
§ 371 (c)(1),
(2) Date: Nov. 23, 2021

(87) PCT Pub. No.: WO2021/060746
PCT Pub. Date: Apr. 1, 2021

(65) Prior Publication Data
US 2022/0212157 A1     Jul. 7, 2022

(30) Foreign Application Priority Data
Sep. 25, 2019 (KR) .................. 10-2019-0118065

(51) Int. Cl.
C07C 67/54 (2006.01)
B01D 19/00 (2006.01)
B01J 19/00 (2006.01)
C07C 67/08 (2006.01)

(52) U.S. Cl.
CPC .............. *C07C 67/54* (2013.01); *B01D 19/00* (2013.01); *B01J 19/0046* (2013.01); *C07C 67/08* (2013.01); *B01J 2219/00452* (2013.01); *B01J 2219/0059* (2013.01)

(58) Field of Classification Search
CPC ...... C07C 67/08; C07C 67/54; B01J 19/0046; B01J 19/00452; B01D 19/00
See application file for complete search history.

(56) References Cited

U.S. PATENT DOCUMENTS

| | | | |
|---|---|---|---|
| 3,839,414 A | 10/1974 | Windle, III et al. | |
| 8,299,292 B2 * | 10/2012 | Yoon | C07C 67/03 560/127 |
| 8,901,344 B2 | 12/2014 | Peters et al. | |
| 9,174,920 B1 | 11/2015 | Panchal et al. | |
| 10,207,978 B2 * | 2/2019 | Schraut | C07C 67/08 |
| 2009/0264674 A1 | 10/2009 | Huang et al. | |
| 2011/0251420 A1 * | 10/2011 | Disteldorf | C07C 67/08 560/99 |
| 2011/0263770 A1 | 10/2011 | Yoon et al. | |
| 2011/0301377 A1 * | 12/2011 | Peters | C07C 67/08 560/99 |

(Continued)

FOREIGN PATENT DOCUMENTS

| | | |
|---|---|---|
| CN | 102256922 A | 11/2011 |
| EP | 3995483 A1 | 5/2022 |

(Continued)

*Primary Examiner* — Yate' K Cutliff
(74) *Attorney, Agent, or Firm* — Bryan Cave Leighton Paisner LLP (57) ABSTRACT

The present disclosure relates to a method for continuously producing a dicarboxylate-based composition and a production system therefor, the method improving a production yield by optimizing process variables of each reactor of a reaction unit in which a plurality of reactors are connected in series.

12 Claims, 3 Drawing Sheets

(56) References Cited

U.S. PATENT DOCUMENTS

| | | |
|---|---|---|
| 2013/0053492 A1 | 2/2013 | Yoon et al. |
| 2014/0288325 A1 | 9/2014 | Yang et al. |
| 2015/0141691 A1 | 5/2015 | Disteldorf et al. |
| 2016/0194267 A1 | 7/2016 | Backes et al. |
| 2016/0264508 A1 | 9/2016 | Smidt et al. |
| 2016/0264509 A1 | 9/2016 | Kaller et al. |
| 2019/0263745 A1 | 8/2019 | Lee et al. |
| 2021/0040026 A1 | 2/2021 | Lee et al. |
| 2022/0220058 A1 | 7/2022 | Jeong et al. |
| 2022/0356144 A1 | 11/2022 | Choo et al. |

FOREIGN PATENT DOCUMENTS

| | | |
|---|---|---|
| JP | 48030046 A | 4/1973 |
| JP | 50100010 A | 8/1975 |
| JP | 63-101346 A | 5/1988 |
| JP | 2012-512231 A | 5/2012 |
| JP | 2012512229 A | 5/2012 |
| JP | 2016-536313 A | 11/2016 |
| JP | 2017502082 A | 1/2017 |
| JP | 2022530520 A | 6/2022 |
| JP | 2022538963 A | 9/2022 |
| KR | 10-1984-0002023 B1 | 11/1984 |
| KR | 10-2010-0042579 A | 4/2010 |
| KR | 10-2011-0101205 A | 9/2011 |
| KR | 10-2014-0115977 A | 10/2014 |
| KR | 10-2016-0055178 A | 5/2016 |
| KR | 10-1663586 B1 | 10/2016 |
| KR | 10-1838815 B1 | 3/2018 |
| KR | 10-2019-0027622 A | 3/2019 |
| KR | 10-2019-0027623 A | 3/2019 |

\* cited by examiner

SYSTEM AND METHOD FOR PRODUCING DIESTER-BASED COMPOSITION

CROSS-REFERENCE TO RELATED APPLICATIONS

This application is a National Phase entry pursuant to 35 U.S.C. § 371 of International Application No. PCT/KR2020/012231, filed on Sep. 10, 2020, and claims the benefit of and priority to Korean Patent Application No. 10-2019-0118065, filed on Sep. 25, 2019, in the Korean Intellectual Property Office, all of which are hereby incorporated by reference in their entirety for all purposes as if fully set forth herein.

TECHNICAL FIELD

Technical Field

The present invention relates to a production system and a production method which increase the production efficiency of a diester-based composition by improving an alcohol reflux process in a process of continuously producing a diester-based composition.

Background Art

Phthalate-based plasticizers had occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248), and are additives used to improve the processability of polyvinyl chloride (hereinafter, referred to as PVC) by imparting flexibility, durability, cold resistance, and the like and lowering viscosity during melting. Phthalate-based plasticizers are introduced into PVC in various contents and used not only for hard products such as rigid pipes, but also for soft products such as food packaging materials, blood bags, and flooring materials since the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may be leaked little by little out of the product and act as a suspected endocrine disruptor (environmental hormone) and a carcinogen to the level of a heavy metal (NR Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, since a report was published in the 1960s in the United States that diethylhexyl phthalate (di-(2-ethylhexyl) phthalate, DEHP), the most used phthalate plasticizer, leaked out of PVC products, global environmental regulations have started to be implemented in addition to various studies on the harmful nature of the phthalate-based plasticizer on human bodies, boosted by increasing interest in environmental hormones in the 1990s.

Thus, in order to respond to environmental hormonal problems and environmental regulations due to the leakage of a phthalate-based plasticizer, di(2-ethylhexyl) phthalate in particular, many researchers have been conducting research in order to develop a new non-phthalate-based alternative plasticizer without phthalic anhydride used in the manufacturing of di(2-ethylhexyl) phthalate, and to develop a phthalate-based plasticizer which may replace di(2-ethylhexyl) phthalate and be used for industrial purposes since the leakage of the plasticizer is suppressed even though it is based on phthalate, as well as to develop a leakage suppression technology which suppresses the leakage of phthalate-based plasticizers, thereby significantly reducing risks to human bodies and which meets environmental standards.

As such, as diester-based plasticizers, the development of materials which are free from environmental problems and which may replace a di(2-ethylhexyl) phthalate having existing environmental problems is actively underway. In addition, research on developing a diester-based plasticizer with excellent physical properties as well as research on equipment for manufacturing the plasticizer have been actively conducted, and there has been a demand for more efficient, more economical and simpler process designs in terms of process design.

Meanwhile, a batch process is being applied in most industrial sites as a process of producing the above diester-based plasticizer. As the batch process, an invention related to a gas-liquid separation system for the reflux of non-reactants and efficient removal of sub-reactants in a reactor (Korean Patent Laid-Open Publication No. 10-2019-0027622) and an invention related to a system integrating facilities of a primary direct esterification reaction and a second trans-esterification reaction in order to simplify facilities of a batch process (Korean Patent Laid-Open Publication No. 10-2019-0027623) have been introduced. However, as a batch process, such inventions have limitations in that there is a limit to the improvement in the amount of reflux or the volume of steam, the productivity is very low, and there is a limit to the technology which may be applied for improvement.

In addition, as a continuous process, an invention related to a process configuring a reaction part by connecting two or more reactors in series (Korean Patent Laid-Open Publication No. 10-1663586) has also been introduced. However, the invention relates to the control of a reaction temperature of a reactor for achieving a target conversion, and there is a limit to the improvement of a process and energy saving.

PRIOR ART DOCUMENT (Patent Document 1) Korean Patent Laid-Open Publication No. 10-2019-0027622
(Patent Document 2) Korean Patent Laid-Open Publication No. 10-2019-0027623
(Patent Document 3) Korean Patent Laid-Open Publication No. 10-1663586

DISCLOSURE OF THE INVENTION

Technical Problem

An aspect of the present invention provides an efficient system and an efficient method for producing a diester-based composition, wherein the condensation of unreacted alcohol in a reflux unit connected to a reactor is performed in two different condensers, which are a pre-condenser and a condenser, in order to reduce the amount of cooling water used in unnecessary condensation, so that the overall efficiency and economic feasibility of a process are improved.

Technical Solution

According to an aspect of the present invention, there is provided a system for producing a diester-based composition, the system including a first reactor in which an esterification reaction of dicarboxylic acid and alcohol is performed, and a first reflux unit connected to the first reactor and selectively separating unreacted alcohol of a mixed gas generated during the reaction and then refluxing the separated unreacted alcohol to the first reactor, wherein the first reflux unit includes 1) a first reflux column directly connected to the first reactor and receiving the mixed gas and unreacted alcohol in a liquid state and then transferring the mixed gas to a first pre-condenser and the unreacted alcohol in a liquid state to the first reactor, 2) the first pre-condenser directly connected to the first reflux column and condensing a portion of the unreacted alcohol of the mixed gas, 3) a gas-liquid separation device directly connected to the first pre-condenser and receiving the mixed gas and the unreacted alcohol in a liquid state and then transferring the mixed gas to a first condenser and the unreacted alcohol in a liquid state to the first reflux column, 4) the first condenser directly connected to the gas-liquid separation device and condensing all of the mixed gas, and 5) a first layer-separator directly connected to the first condenser and separating alcohol and water in a condensate and then transferring an alcohol layer to the gas-liquid separation device and discharging a water layer.

According to another aspect of the present invention, there is provided a method for producing a diester-based composition, the method including subjecting dicarboxylic acid and alcohol to an esterification reaction S1, partially condensing a mixed gas generated during the esterification reaction to separately obtain unreacted alcohol in a liquid state and the remaining mixed gas S2, and condensing all of the remaining mixed gas and then performing layer separation to obtain a water layer and an alcohol layer S3, wherein the unreacted alcohol in a liquid state obtained in Step S2 and the alcohol layer obtained in Step S3 are reused as the alcohol in Step S1.

Advantageous Effects

In a production system and a production method of the present invention, refluxed alcohol is divided and condensed, so that the overall amount of energy used for condensation is reduced, and when a plurality of reactors are used, the reflux means of the frontmost reactor is shared as the reflux means of subsequent reactors, so that a process can be simplified.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

System for Producing Diester-Based Composition

Figure 1:
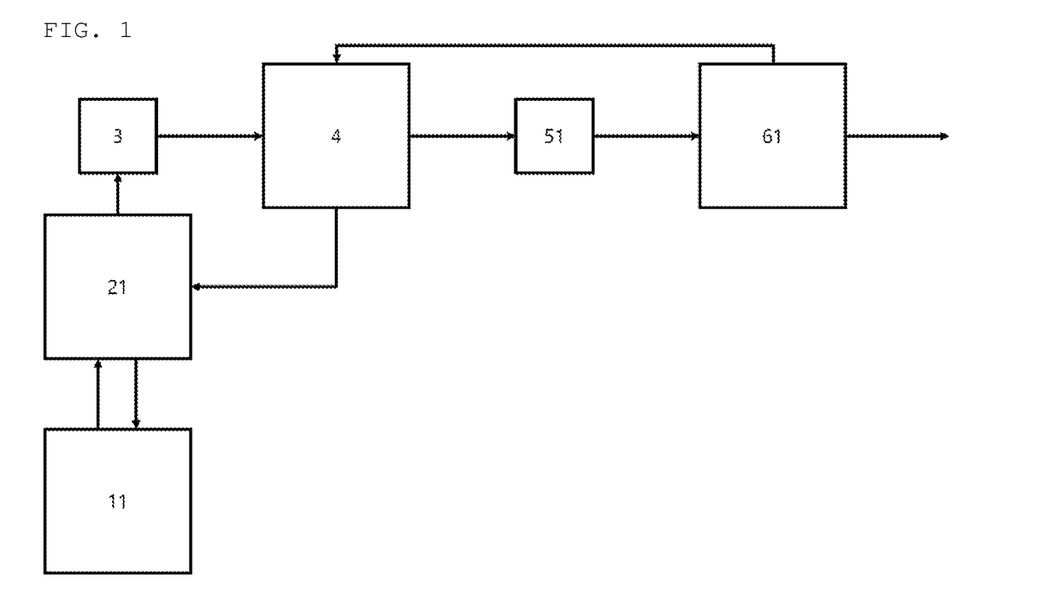
FIG. 1 is a simplified diagram of a first reactor part in a system for producing a diester-based composition of the present invention.

As illustrated in FIG. 1, the present invention provides a system for producing a diester-based composition, the system including a first reactor 11 in which an esterification reaction of dicarboxylic acid and alcohol is performed, and a first reflux unit connected to the first reactor and selectively separating unreacted alcohol of a mixed gas generated during the reaction and then refluxing the separated unreacted alcohol to the first reactor, wherein the first reflux unit includes 1) a first reflux column 21 directly connected to the first reactor and receiving the mixed gas and unreacted alcohol in a liquid state and then transferring the mixed gas to a first pre-condenser and the unreacted alcohol in a liquid state to the first reactor, 2) the first pre-condenser 3 directly connected to the first reflux column and condensing a portion of the unreacted alcohol of the mixed gas, 3) a gas-liquid separation device 4 directly connected to the first pre-condenser and receiving the mixed gas and the unreacted alcohol in a liquid state and then transferring the mixed gas to a first condenser and the unreacted alcohol in a liquid state to the first reflux column, 4) the first condenser 51 directly connected to the gas-liquid separation device and condensing all of the mixed gas, and 5) a first layer-separator 61 directly connected to the first condenser and separating alcohol and water in a condensate and then transferring an alcohol layer to the gas-liquid separation device and discharging a water layer.

A diester-based composition is prepared by an esterification reaction of dicarboxylic acid and alcohol, which are reaction raw materials. Specifically, through the esterification reaction, a carboxyl group of the dicarboxylic acid and a hydroxy group of the alcohol are condensed to form an ester bond, and as a result, water is formed as a by-product. Meanwhile, although it may vary depending on the specific type of dicarboxylic acid and alcohol which are reaction raw materials, an esterification reaction is performed at a temperature of approximately 130 to 250° C. Therefore, the vaporization of the alcohol, which is a reaction raw material, and water, which is a by-product, may occur during the reaction. Particularly, since the vaporization of alcohol lowers the concentration of alcohol, the overall reaction rate is lowered, thereby reducing the efficiency of an overall production process. Therefore, It is necessary to improve the efficiency of the production process by recovering a mixed gas including water and alcohol both in a gaseous state generated during the reaction, and selectively re-introducing the alcohol in the mixed gas to the reactor. To this end, most diester-based composition production systems are provided with a reflux facility connected to a reactor.

A typical reflux facility includes a reflux column to introduce a liquid to a reactor and introduce a gas to a condenser separately provided. A mixed gas including water and alcohol both in a gaseous state is transferred to the condenser through the reflux column, and all of the mixed gas is condensed in the condenser to form a mixed liquid of water and alcohol. Water and alcohol have different chemical properties, and thus, can be easily separated using equipment such as a layer separator. Separated alcohol is discharged back to the reactor through the reflux column and water remaining in the mixed liquid is discharged as wastewater. A typical reflux facility as described above may solve the problem that there is a large amount of alcohol not participating in the reaction since alcohol vaporizes during the above-described reaction, but has a problem in that a large amount of energy is additionally consumed for condensing water and alcohol since vaporized water and alcohol are all condensed and then alcohol is separated therefrom and introduced. Therefore, a lot of efforts have been put into reducing energy consumed in a reflux process while maintaining or improving the efficiency of reflux. The present invention has been completed for the same purpose of reducing energy consumed in a reflux process.

Specifically, the system for producing a diester-based composition provided by the present invention includes a first reactor and a first reflux unit having a first reflux column, a first pre-condenser, a gas-liquid separation device, a first condenser, and a first layer separator. The reactor is not particularly limited as long as it is used in an esterification reaction. It is preferable that the reactor is a continuous reactor in that the system for producing a diester-based composition of the present invention can be continuously operated. For example, a Continuous Stirred-Tank Reactor (CSTR) can be applied as the reactor. The system for producing a diester-based composition of the present invention can include a singular reactor, or a plurality of reactors, preferably 2 to 10 reactors connected in series. When the system includes a single reactor, the reactor is the first reactor, and when the system includes a plurality of reactors, the first reactor refers to a reactor disposed at the frontmost end of the plurality of reactors connected in series.

The first reflux unit is to perform the reflux described above, particularly the reflux of the first reactor. In describing components of the present invention, a description such as "an X-th" indicates that a corresponding component is applied to an X-th reactor, and the same can be applied to a reflux column, a pre-condenser, a condenser, or a layer separator to be described later. The first reflux unit includes 1) a first reflux column directly connected to the first reactor and receiving the mixed gas and unreacted alcohol in a liquid state and then transferring the mixed gas to a first pre-condenser and the unreacted alcohol in a liquid state to the first reactor, 2) the first pre-condenser directly connected to the first reflux column and condensing a portion of the unreacted alcohol of the mixed gas, 3) a gas-liquid separation device directly connected to the first pre-condenser and receiving the mixed gas and the unreacted alcohol in a liquid state and then transferring the mixed gas to a first condenser and the unreacted alcohol in a liquid state to the first reflux column, 4) the first condenser directly connected to the gas-liquid separation device and condensing all of the mixed gas, and 5) a first layer-separator directly connected to the first condenser and separating alcohol and water in a condensate and then transferring an alcohol layer to the gas-liquid separation device and discharging a water layer.

The first reflux column is directly connected to the first reactor, and is for receiving a mixture of alcohol and water, that is, a mixed gas, which are in a gaseous state and generated during the reaction, and for receiving alcohol liquefied through a reflux process, that is, unreacted alcohol in a liquid state, as well. The mixed gas and the unreacted alcohol in a liquid state which are be received in the first reflux column are in different phases from each other, and thus, can be easily separated. The mixed gas is transferred to the first pre-condenser to be subjected to a subsequent reflux process, and the unreacted alcohol in a liquid state is transferred to the first reactor to be used as a reaction raw material again. The shape or type of the first reflux column is not particularly limited. Any reflux column can be used as long as it can separate the mixed gas and the unreacted alcohol in a liquid state. Meanwhile, the reflux column is preferable connected to an upper portion of a reactor in that the reflux column is for receiving a mixed gas generated in the reactor.

The first pre-condenser is for condensing a portion of the mixed gas transferred from the first reflux column. Unlike in the prior art, in the present invention, the mixed gas is condensed over two stages, and the condensation of a first stage of the two stages is performed in a pre-condenser. In the pre-condenser, 50 to 95%, preferably 70 to 95% of the mixed gas is condensed. Since the boiling point of water is lower than the boiling point of alcohol, if the temperature at which condensation is performed is set to a temperature between the boiling point of water and the boiling point of alcohol, alcohol can be selectively condensed. Accordingly, in a condensate obtained through the pre-condenser, unreacted alcohol in a liquid state and a mixed gas containing unreacted alcohol in a gaseous state which has not been condensed and water are included. The first pre-condenser is not particularly limited as long as it can adjust the temperature at which condensation is performed. For example, a heat exchanger and the like for performing heat exchange through cooling water can be included as the first pre-condenser. The unreacted alcohol in a liquid state which has passed through the first pre-condenser and the mixed gas are transferred to a subsequent gas-liquid separation device.

The gas-liquid separation device is for separating a mixed gas and unreacted alcohol in a liquid state. Unreacted alcohol in a gaseous state remaining in the mixed gas can be liquefied and separated through a subsequent first condenser and then a first layer separator to be re-introduced to the gas-liquid separation device. Thus, the gas-liquid separation device can serve to collect all recovered unreacted alcohol in a liquid state and introduce the same into the first reflux column. The shape or type of the gas-liquid separation device is not particularly limited. For example, a gas-liquid separation device in a drum form can be used. When gas-liquid separation is performed, a liquid is positioned at a lower portion and a gas is positioned at an upper portion, so that it is preferable that an upper portion of the gas-liquid separation device is connected to the first condenser and a lower portion thereof is connected to the first reflux column.

A mixed gas separated from the gas-liquid separation device is transferred to the first condenser. In the first condenser, all of the mixed gas is condensed in the same manner as in the prior art. Therefore, as a result, a mixture in a liquid state including water and alcohol is formed. The first condenser can be the same as or different from the first pre-condenser described above, and the shape or type of the first condenser is not particularly limited as in the case of the first pre-condenser. The formed mixture in a liquid state is transferred to the first layer separator.

In the first layer separator, the layer separation of alcohol and water is performed. Alcohol and water have different chemical properties, and thus, the layer separation thereof can be easily achieved. An alcohol layer among separated layers is discharged to the gas-liquid separation device to be re-used as a reaction raw material, and a water layer is discharged to be treated as wastewater. The shape or type of the layer separator is not also particularly limited, and any layer separator which can smoothly perform the layer separation of alcohol and water can be used.

Those skilled in the art may practice the present invention by adding components other than the components described above to the extent that problem solving means of the present invention are applied as they are. For example, a pre-mixer and the like can be applied for the uniform mixing of alcohol and dicarboxylic acid which are reaction raw materials, or a pump for the smooth transfer between each component can be additionally applied. It is apparent that the additional implementation of such components is also included in the scope of the invention.

Meanwhile, as described above, the system for producing a diester-based composition of the present invention can further include an additional reactor other than the first reactor. For example, a second reactor 12 or an N-th reactor can be further included. The second reactor 12 to the N-th reactor can be connected in series to a rear end of the first reactor, and it is preferable that N is an integer of 2 to 10. When the number of reactors increases, there is an advantage in that it is possible to control process variables in more detail. However, when considering that more space additionally required to install reactors in proportion to the increasing number of reactors and that it becomes difficult to properly operate an entire production process, it is preferable that the total number of reactors, that is, N, is 2 to 10, more preferably 2 to 5.

As in the case of the first reactor, the vaporization of unreacted alcohol and water occurs in the N-th reactor. Therefore, the system for producing a diester-based composition of the present invention can further include reflux units for the second reactor to the N-th reactor, that is, a second reflux unit to an N-th reflux unit. That is, the system for producing a diester-based composition of the present invention can include an X-th reflux unit, and X is an integer of 2 to N.

Specifically, the X-th reflux unit can include an X-th reflux column 22 as in the case of the first reflux column. The X-th reflux column is directly connected to an X-th reactor and receives a mixed gas and unreacted alcohol in a liquid state and then transfer the unreacted alcohol in a liquid state to the X-th reactor.

Figure 2:
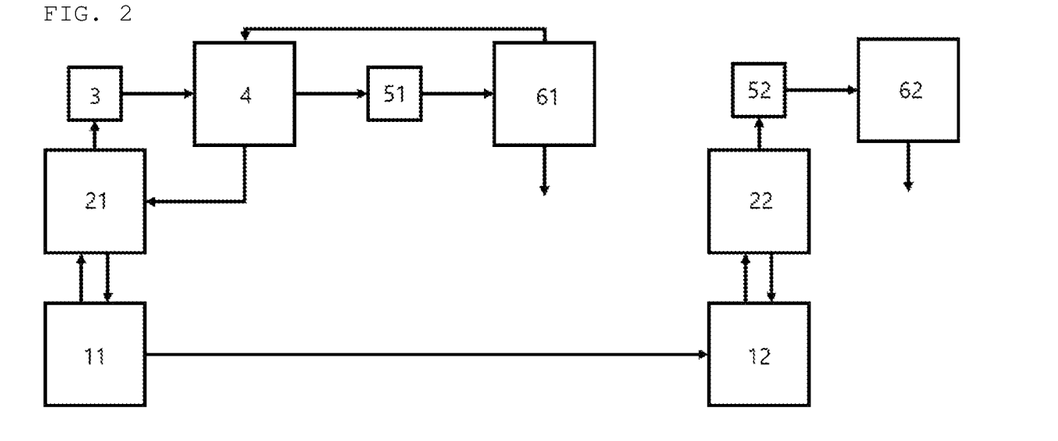
FIGS. 2 to 4 are simplified diagrams of a system for producing a diester-based composition according to Examples 1 to 3 of the present invention.

In addition, as illustrated in FIG. 2, the X-th reflux unit can further include an X-th condenser 52 directly connected to the X-th reflux column and condensing all of the mixed gas and an X-th layer-separator 62 directly connected to the X-th condenser and separating alcohol and water in a condensate and then transferring an alcohol layer to the X-th reflux column and discharging a water layer. The X-th reflux unit may include only one condenser different from the case of the first reflux unit. It is also possible to design the X-th reflux unit to be the same as the first reflux unit. However, when considering that the amount of remaining reaction raw materials decreases going toward a rear end of a plurality of reactors connected in series, and thus, the amount of vaporized alcohol and water also decreases, it is efficient to design the X-th reflux unit to include only one condenser as in the prior art.

Figure 3:
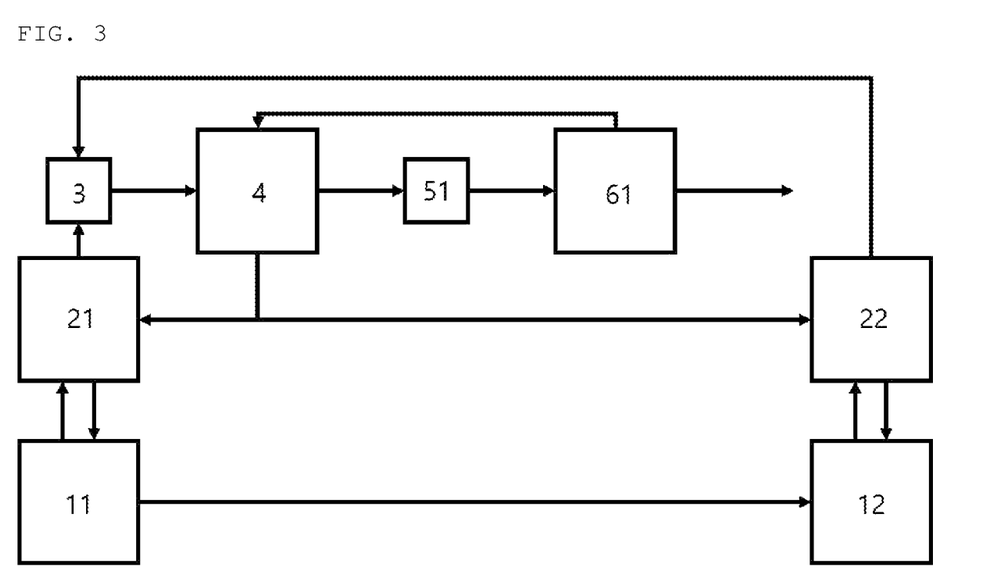
Figure 4:
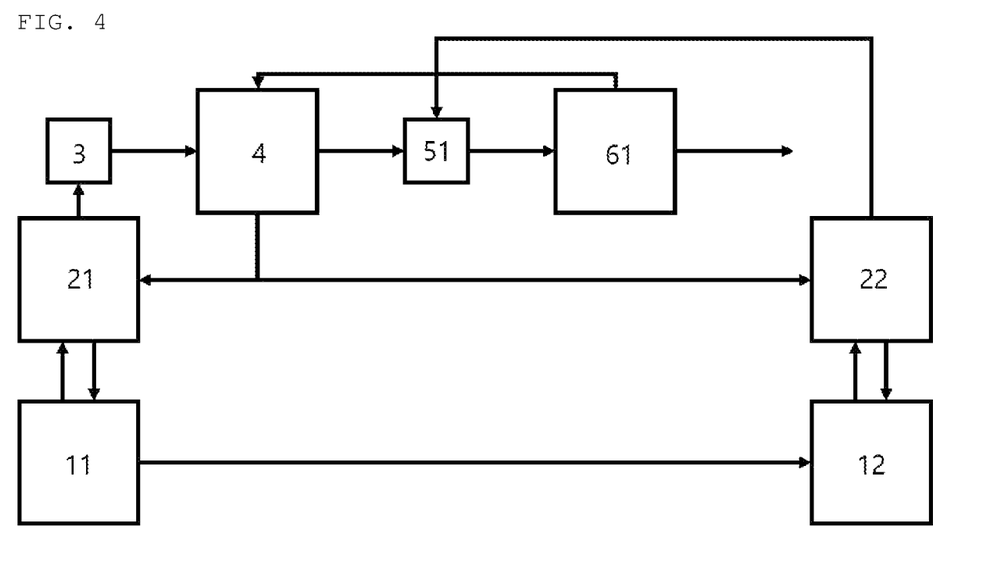
Figure 5:
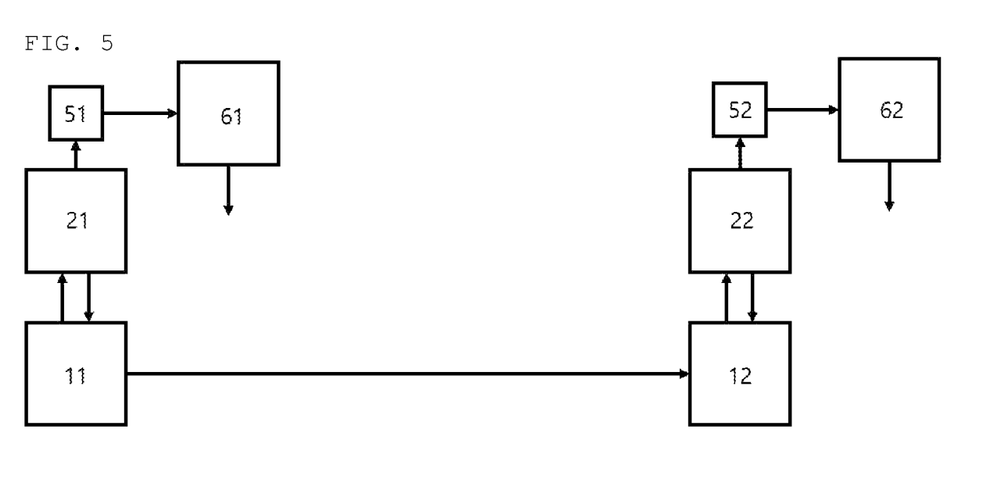
FIG. 5 is a simplified diagram of a system for producing a diester-based composition of Comparative Example, wherein a first pre-condenser and a gas-liquid separation device in a system for producing a diester-based composition of the present invention are not included.

Alternatively, as illustrated in FIG. 3 and FIG. 4, the x-th reflux unit may only include a reflux column and not a condenser and a layer separator. In this case, the X-th reflux column can be additionally connected to the gas-liquid separation device and the first pre-condenser of the first reflux unit as shown in FIG. 3, or can be additionally connected to the gas-liquid separation device and the first condenser of the first reflux unit as shown in FIG. 4, and transfer the mixed gas to the first pre-condenser and receive a portion of unreacted alcohol in a liquid state which is transferred from the gas-liquid separation device to the first reflux column. As described above, when a separate condenser or a separate layer separator is not applied to the X-th reflux unit, but instead, the pre-condenser and the gas-liquid separation device of the first reflux unit are shared, the size of a device is also reduced, so that there is an advantage in that a process can be simplified.

Method for Producing Diester-Based Composition

The present invention provides a method for producing a diester-based composition using the system for producing a diester-based composition described above. Specifically, the method includes subjecting dicarboxylic acid and alcohol to an esterification reaction S1, partially condensing a mixed gas generated during the esterification reaction to separately obtain unreacted alcohol in a liquid state and the remaining mixed gas S2, and condensing all of the remaining mixed gas and then performing layer separation to obtain a water layer and an alcohol layer S3, wherein the unreacted alcohol in a liquid state obtained in Step S2 and the alcohol layer obtained in Step S3 are reused as the alcohol in Step S1.

Step S1 is continuously performed in a first reactor or in the first reactor to an N-th reactor, and is a step of forming an ester compound by reacting dicarboxylic acid and alcohol. The esterification reaction can be performed at 130 to 250° C., preferably 140 to 240° C., and more preferably 150 to 230° C. When a reaction temperature is lower than the above, energy required for the reaction is not sufficiently supplied, and thus, a sufficient conversion rate may not be achieved. When higher than the above, the vaporization of dicarboxylic acid or alcohol, which are reaction raw materials, occurs in a large amount, and thus, the reaction rate is lowered, and also, a sufficient amount of reaction product may not be obtained.

The esterification reaction can be performed in the presence of an acidic catalyst. A catalyst which can be used can be one or more selected from an acidic catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfuric acid, a metal salt such as aluminum lactate, lithium fluoride, potassium chloride, cesium chloride, calcium chloride, iron chloride, and phosphoric acid, a metal oxide such as heteropoly acid, an organic metal such as a natural/synthetic zeolite, a cation and an anion exchange resin, tetraalkyl titanate, and a polymer thereof, and the like. Particularly, the catalyst used in the production method of the present invention may preferably be tetraalkyl titanate. As the tetraalkyl titanate, TiPT, TnBT, TEHT, or the like can be used, and it is preferable to use tetraalkyl titanate having the same alkyl group as the alkyl group of alcohol, which is a reaction raw material, as a ligand. As described above, when a catalyst having the same alkyl group as a ligand is used, catalyst by-products which may be generated in a subsequent process are not generated, or can be easily controlled.

The catalyst can be pre-mixed with dicarboxylic acid and alcohol, which are reaction raw materials, and then introduced into a first reactor, or can be directly introduced into the first reactor through a separate line from the dicarboxylic acid and the alcohol. In terms of the uniformity of the reaction, it is preferable that the catalyst is pre-mixed with dicarboxylic acid and alcohol and then introduced.

The dicarboxylic acid, which is a reaction raw material, can include one or more selected from the group consisting of phthalic acid, isophthalic acid, terephthalic acid, and cyclohexane dicarboxylic acid, and the alcohol can be one or more alcohols selected from alcohols having 3 to 12 alkyl carbon atoms. The alcohol includes all of linear, branched, or cyclic alcohols, and is preferably a primary alcohol. When such reaction materials are used, the production method of the present invention can be more smoothly applied, and a diester-based composition produced thereby can more excellently serve as a plasticizer.

Step S2 is performed in a first pre-condenser and in a gas-liquid separation device, and is a step of condensing a portion of a mixed gas containing unreacted alcohol in a gaseous state and water to form a gas-liquid mixture and then performing gas-liquid separation. The amount of the mixed gas partially condensed in the present step is about 50 to 95%, preferably 70 to 95% of the total mixed gas. When partially condensed in the above range, the energy efficiency of an entire production process can be further increased. The partial condensation can be performed at a temperature of 100 to 190° C., preferably 130 to 160° C. When partially condensed in the above temperature range, the selective condensation of alcohol can be more facilitated, and the content of moisture in the alcohol may be low. Unreacted alcohol in a liquid state separated in the present invention can be re-used as the alcohol of Step S1.

Step S3 can be performed in a first condenser and a layer separator, and is a step of condensing all of the mixed gas remaining after the partial condensation to perform layer separation of alcohol and water and then discharging a water layer as wastewater and re-using an alcohol layer as a reaction raw material. The alcohol layer separated in the present step can also be re-used as the alcohol of Step S1.

EXAMPLES

Hereinafter, preferred Examples are presented to aid in understanding of the present invention. However, the following Examples are merely illustrative of the present invention and are not intended to limit the scope of the present invention.

A system for producing a diester-based composition was configured as shown in each of FIGS. 2 to 5, and terephthalic acid was selected as the dicarboxylic acid and octanol was selected as the alcohol. The steam usage amount for each case was calculated using Aspen Plus, which is a chemical process simulation program. The system for producing a diester-based composition configured as shown in each of FIGS. 2 to 4 was set to Examples 1 to 3, respectively. The system for producing a diester-based composition of FIG. 5, which does not include a first pre-condenser and a gas-liquid separation device, was set to Comparative Example.

The calculation results are shown in Table 1 below

TABLE 1

|  | Steam usage amount of first reactor (kg/hr) | Steam usage amount of second reactor (kg/hr) | Total steam usage amount (kg/hr) | Steam usage rate of first reactor compared to Comparative Example (%) | Steam usage rate of second reactor compared to Comparative Example (%) | Total steam usage rate compared to Comparative Example (%) |
|---|---|---|---|---|---|---|
| Comparative Example | 4706 | 560 | 5266 | — | — | — |
| Example 1 | 4166 | 506 | 4672 | 89 | 90 | 89 |
| Example 2 | 4166 | 506 | 4672 | 89 | 90 | 89 |
| Example 3 | 4294 | 496 | 4789 | 91 | 88 | 91 |

From the results above, it can be confirmed that the production system of diester-based composition of the present invention is energy efficient since the steam usage amount can be reduced compared to Comparative Example.

REFERENCE SIGNS

11: a first reactor
12: a second reactor
21: a first reflux column
22: a second reflux column
3: a first pre-condenser
4: a gas-liquid separation device
51: a first condenser
52: a second condenser
61: a first layer-separator
62: a second layer-separator

The invention claimed is:

1. A system for producing a diester-based composition, the system comprising:
    a first reactor in which an esterification reaction of dicarboxylic acid and alcohol is performed;
    a first reflux unit connected to the first reactor and selectively separating unreacted alcohol from a mixed gas generated during the esterification reaction, and then refluxing the separated unreacted alcohol to the first reactor, wherein the first reflux unit comprises:
    1) a first reflux column directly connected to the first reactor and receiving the mixed gas and unreacted alcohol in a liquid state and then transferring the mixed gas to a first pre-condenser and the unreacted alcohol in a liquid state to the first reactor;
    2) the first pre-condenser directly connected to the first reflux column and condensing a portion of the unreacted alcohol in the mixed gas from the first reflux column;
    3) a gas-liquid separation device directly connected to the first pre-condenser and receiving the mixed gas and the unreacted alcohol in a liquid state which is condensed from the portion of the unreacted alcohol, and then transferring the mixed gas to a first condenser and the unreacted alcohol in a liquid state to the first reflux column;

4) the first condenser directly connected to the gas-liquid separation device and condensing the mixed gas from the gas-liquid separation device; and
5) a first layer-separator directly connected to the first condenser and separating alcohol and water in a condensate and then transferring an alcohol layer to the gas-liquid separation device and discharging a water layer.

2. The system of claim 1, further comprising a second reactor to an N-th reactor, wherein:
the second reactor to the N-th reactor are connected in series to a rear end of the first reactor; and
N is an integer of 2 to 10.

3. The system of claim 2, further comprising an X-th reflux unit connected to an X-th reactor and selectively separating unreacted alcohol from a mixed gas generated during the esterification reaction and then refluxing the separated unreacted alcohol to the X-th reactor, wherein X is an integer of 2 to N.

4. The system of claim 3, wherein the X-th reflux unit comprises an X-th reflux column directly connected to the X-th reactor and receiving the mixed gas and unreacted alcohol in a liquid state and then transferring the unreacted alcohol in a liquid state to the X-th reactor.

5. The system of claim 4, wherein the X-th reflux unit comprises:
an X-th condenser directly connected to the X-th reflux column and condensing all of the mixed gas; and
an X-th layer-separator directly connected to the X-th condenser and separating alcohol and water in a condensate and then transferring an alcohol layer to the X-th reflux column and discharging a water layer.

6. The system of claim 4, wherein the X-th reflux column is additionally connected to the first pre-condenser and the gas-liquid separation device, and transfers the mixed gas to the first pre-condenser and receives a portion of unreacted alcohol in a liquid state which is transferred from the gas-liquid separation device to the first reflux column.

7. The system of claim 1, wherein the first reflux column is connected to an upper portion of the first reactor.

8. The system of claim 1, wherein the gas-liquid separation device is connected to an upper portion of the first reflux column.

9. A method for producing a diester-based composition, the method comprising:
subjecting dicarboxylic acid and alcohol to an esterification reaction (S1);
partially condensing a mixed gas generated during the esterification reaction to separately obtain unreacted alcohol in a liquid state and the remaining mixed gas (S2); and
condensing all of the remaining mixed gas and then performing layer separation to obtain a water layer and an alcohol layer (S3),
wherein the unreacted alcohol in a liquid state obtained in Step S2 and the alcohol layer obtained in Step S3 are reused as the alcohol in Step S1.

10. The method of claim 9, wherein the amount of the mixed gas partially condensed in Step S2 is 50 to 95% of the total mixed gas.

11. The method of claim 9, wherein the partial condensation in Step S2 is performed at a temperature of 100 to 190° C.

12. The method of claim 9, wherein:
the dicarboxylic acid comprises one or more selected from the group consisting of terephthalic acid, phthalic acid, isophthalic acid, and cyclohexane dicarboxylic acid; and
the alcohol is one or more selected from alcohols having 3 to 12 alkyl carbon atoms.

* * * * *